(12) United States Patent
Lee (10) Patent No.: US 12,222,290 B2
(45) Date of Patent: Feb. 11, 2025

(54) DETECTION METHOD AND DETECTION PAD

(71) Applicant: QSTAG Co., Ltd., Gunpo-si (KR)

(72) Inventor: Dong Hoon Lee, Suwon-si (KR)

(73) Assignee: QSTAG Co., LTD., Gunpo-si (KR)

( * ) Notice: Subject to any disclaimer, the term of this patent is extended or adjusted under 35 U.S.C. 154(b) by 372 days.

(21) Appl. No.: 17/617,249

(22) PCT Filed: Jun. 3, 2020

(86) PCT No.: PCT/KR2020/007183
§ 371 (c)(1),
(2) Date: Dec. 7, 2021

(87) PCT Pub. No.: WO2020/246786
PCT Pub. Date: Dec. 10, 2020

(65) Prior Publication Data
US 2022/0236190 A1    Jul. 28, 2022

(30) Foreign Application Priority Data
Jun. 7, 2019   (KR) .................. 10-2019-0067144

(51) Int. Cl.
*G01N 21/78*    (2006.01)
*G01N 33/52*    (2006.01)
(Continued)

(52) U.S. Cl.
CPC ........... *G01N 21/78* (2013.01); *G01N 33/521* (2013.01); *G06T 7/90* (2017.01); *H04N 9/64* (2013.01); *G06T 2207/10024* (2013.01)

(58) Field of Classification Search
CPC ........ G01N 21/78; G01N 33/521; G06T 7/90; G06T 2207/10024; H04N 9/64
See application file for complete search history.

(56) References Cited

U.S. PATENT DOCUMENTS 4,827,944 A * 5/1989 Nugent ................ G01N 33/521
                                                                604/404
2006/0140818 A1* 6/2006 Sakamoto ............ G01N 33/523
                                                                422/400
(Continued)

FOREIGN PATENT DOCUMENTS

JP          2015-533211 A      11/2015
KR    10-2014-0074256 A       6/2014
(Continued)

OTHER PUBLICATIONS

Written Opinion issued on Sep. 11, 2020 in counterpart Korean PCT International Application No. PCT/KR2020/007183 (6 pages in English, 7 pages in Korean).
(Continued)

*Primary Examiner* — Syed Haider
(74) *Attorney, Agent, or Firm* — NSIP Law (57) ABSTRACT

A detection method according to the present embodiment comprises the steps of (a) photographing a first reference color area indicated by a first reference color, a second reference color area indicated by a second reference color, and a detection region reacting with a target so as to change color, (b) converting a photography result into a single element, (c) extracting a single element gradation value from the converted photography result, (d) converting the extracted single element gradation value into a standard gradation value, and (e) detecting the concentration of the target from the standard gradation value.

20 Claims, 11 Drawing Sheets

(51) Int. Cl.
  *G06T 7/90*        (2017.01)
  *H04N 9/64*        (2023.01)

(56) References Cited

U.S. PATENT DOCUMENTS

| | | | |
|---|---|---|---|
| 2014/0072189 A1 | 3/2014 | Jena et al. | |
| 2014/0154789 A1* | 6/2014 | Polwart ............. | G01N 21/8483 |
| | | | 422/403 |
| 2015/0241358 A1* | 8/2015 | Burg ................... | G01N 21/272 |
| | | | 422/402 |
| 2016/0125600 A1* | 5/2016 | Lee .................... | G01N 21/8483 |
| | | | 382/128 |
| 2017/0097342 A1* | 4/2017 | Sundvor ............ | G01N 33/5308 |
| 2021/0164963 A1 | 6/2021 | Lee et al. | |

FOREIGN PATENT DOCUMENTS

| | | | | |
|---|---|---|---|---|
| KR | 10-2016-0052442 A | 5/2016 | | |
| KR | 101749627 B1 * | 5/2016 | ............. | G01N 33/52 |
| KR | 10-1802469 B1 | 11/2017 | | |

OTHER PUBLICATIONS

International Search Report Issued on Sep. 11, 2020 in counterpart Korean PCT International Application No. PCT/KR2020/007183. (2 pages in English, 3 pages in Korean).

\* cited by examiner

| PROTEIN (mg/ml) | STANDARD GRADATION VALUE |
|---|---|
| 0 | 214.38929 |
| 15 | 193.15062 |
| 30 | 183.50921 |
| 100 | 155.00588 |
| 300 | 141.32002 |
| 1000 | 130.45326 |

| HYROGEN ION CONCENTRATION (pH) | STANDARD GRADATION VALUE |
|---|---|
| 6 | 172.14416 |
| 6.5 | 167.23096 |
| 7 | 128.43282 |
| 8 | 52.78474 |
| 9 | 43.4767 |

| GLUCOSE CONCENTRATION (mg/ml) | STANDARD GRADATION VALUE |
|---|---|
| 0 | 170.32433 |
| 100 | 121.18083 |
| 250 | 76.17331 |
| 500 | 30.09501 |
| 1000 | 52.05627 |

| OCCULT BLOOD (RBC/ul) | STANDARD GRADATION VALUE |
|---|---|
| 0 | 216.06225 |
| 10 | 178.23825 |
| 50 | 70.76191 |
| 250 | 12.79828 |

DETECTION METHOD AND DETECTION PAD

CROSS-REFERENCE TO RELATED APPLICATION

This application is a U.S. National Stage Application of International Application No. PCT/KR2020/007183, filed on Jun. 3, 2020 which claims priority to Korean Patent Application No. 10-2019-0067144, filed on Jun. 7, 2019 and all the benefits accruing therefrom under the priority, the content of which in their entireties are herein incorporated by reference.

TECHNICAL FIELD

The present invention relates to a detection method and detection pad.

BACKGROUND ART

Abnormalities in the body of humans and animals can be detected with high accuracy by detecting the concentration of a substance contained in a body fluid in the living body. An example of detecting a body fluid component is a urine test. When the subject provides urine to a patch containing an indicator, a component in the urine reacts with the indicator such that the color is changed. The changed color is compared with a reference color in a colorimetric table to detect whether the corresponding component is present and/or the concentration of the corresponding component. Another example is a pregnancy test kit which is commonly used. During pregnancy, human chorionic gonadotropin (hCG) is excreted in the urine. Since the pregnancy test kit has a receptor that directly binds to hCG, the receptor binds to hCG such that a predetermined shape and color are displayed.

DISCLOSURE

Technical Problem

A color displayed by a pad that detects a target varies depending on the concentration of the target, and thus a colorimetric table shows various colors depending on the target concentration. However, in many cases, a color obtained by providing a subject's body fluid to an indicator does not exactly correspond to a color in a colorimetric table, and the color may be misrecognized according to surroundings such that accurate detection may be difficult. Further, the test is conducted only once, and thus it is difficult for the subject to be immediately aware of a history and a current change compared to the past.

The present invention is directed to providing a device for detecting whether a target substance is present and/or for detecting the concentration of the target substance.

Technical Solution

One aspect of the present invention provides a detection method including (a) photographing a first reference color area displayed in a first reference color, a second reference color area displayed in a second reference color, and a detection area of which a color is changed in response to a target, (b) converting a photography result into a single factor, (c) extracting a single factor gradation value from the converted photography result, (d) converting the extracted single factor gradation value into a standard gradation value, and (e) detecting a concentration of the target from the standard gradation value.

Another aspect of the present invention provides a detection pad for testing a target in a fluid, the detection pad including a machine-readable code displayed in a first reference color, a second reference color area used to remove an influence of a color change caused by the fluid, and a detection area including a reagent of which a color is changed in response to the target.

Advantageous Effects

According to the present embodiment, it is possible to quantitatively detect a target in a fluid without using a colorimetric table and also to store a past history and the like by datafying the detected target.

MODES OF THE INVENTION

Figure 1:
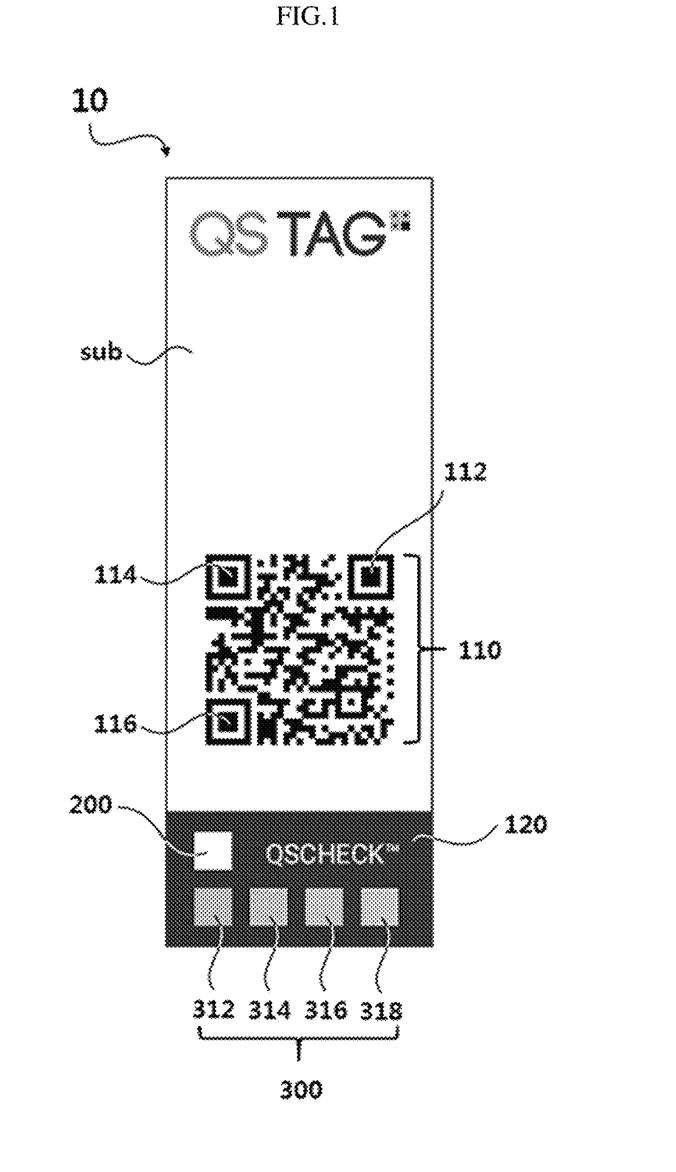
FIG. 1 illustrates an embodiment of a detection pad according to the present embodiment.
Figure 2:
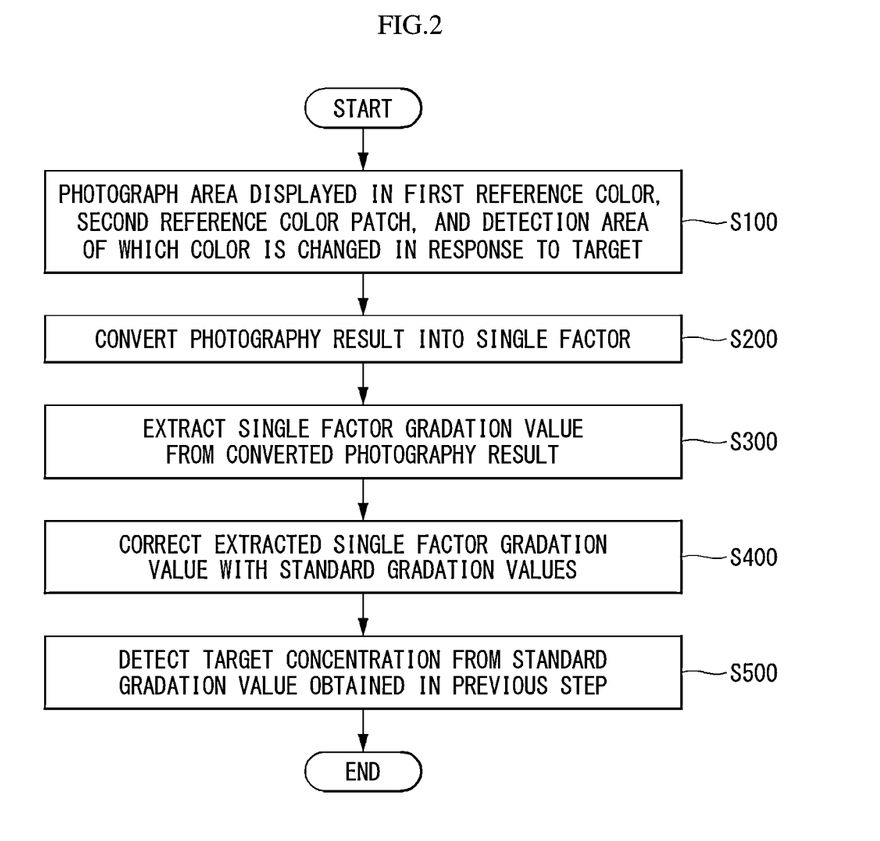
FIG. 2 is a flowchart illustrating the overview of a detection method according to the present embodiment.

Hereinafter, embodiments of a detection pad according to the present embodiment will be described with reference to the accompanying drawings. FIG. 1 illustrates an embodiment of a detection pad 10 according to the present embodiment. FIG. 2 is a flowchart illustrating the overview of a detection method according to the present embodiment.

In the embodiment illustrated in FIG. 1, a first reference color area displayed in a first reference color may be any one or more of a quick response (QR) code 110 displayed in the first reference color and a predetermined area 120 displayed in the first reference color. In an embodiment, the QR code 110 may be displayed in a quadrangle. The QR code 110 may include orientation markers 112, 114, and 116 that are located at three vertices of the quadrangle. The QR code 110 may display the classification of the detection pad 10, a detection target of the detection pad, the number of reagent patches included in a detection area 300, and the like.

The area 120 displayed in the first reference color may be a predetermined area displayed in the first reference color on a substrate sub. According to another embodiment not shown in the drawing, the first reference color area may include letters, numerals, etc. displayed in the first reference color and further include designs and the like. As the embodiment, the first reference color may be black.

In the embodiment, the detection pad 10 may be formed on the substrate sub. As an example, the substrate may be a white paper, and the QR code 110 and/or the first reference color area 120 may be printed and formed on the substrate sub.

The second reference color area 200 may be used to remove color casts caused by surroundings and lighting during photography and coloration by a fluid including a target as will be described below and may be formed in a second reference color. As the embodiment, when the substrate sub is white, a predetermined area of the substrate sub may be determined as the second reference color area 200. In another embodiment, as the second reference color area 200, a white patch, into which the color of a fluid may permeate, may be attached to a predetermined area of the substrate sub. As the embodiment, the second reference color may be white.

The detection area 300 may include one or more reagent patches, and the reagent patches include a reagent of which a color is changed in response to the target included in a fluid. As the embodiment, the reagent may react with the target in a fluid such that the degree of coloration may vary depending on the concentration of the target. As an example, the reagent may be a reagent of which a color is changed according to glucose in a fluid, protein in a fluid, hydrogen ions in a fluid, occult blood in a fluid, bilirubin in a fluid, urobilinogen in a fluid, ketone bodies in a fluid, nitrides in a fluid, the specific gravity of a fluid, and white blood cells in a fluid. As an example, the fluid is a body fluid of a human or animal and may be any one of blood, urine, saliva, and sweat.

In the embodiment illustrated in FIG. 1, the detection area 300 may include four reagent patches 312, 314, 316, and 318, each of which may vary in the degree of color change according to the concentration of glucose in urine, protein in urine, hydrogen ions in urine, or occult blood in urine In an embodiment not shown in the drawing, the detection area may include 10 reagent patches, each of which may vary in the degree of color change according to glucose in urine, protein in urine, hydrogen ions in urine, or occult blood in urine, bilirubin in urine, urobilinogen in urine, ketone bodies in urine, nitrides in urine, the specific gravity of urine, or the concentration of white blood cells in urine.

Figure 3:
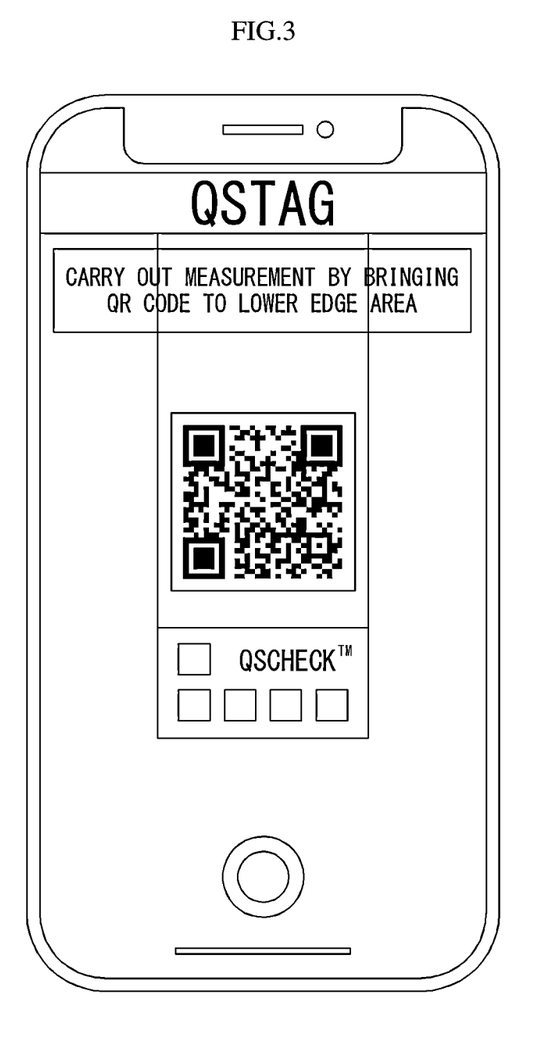
FIG. 3 is a diagram illustrating a state of a portable terminal photographing the detection pad according to the present embodiment.

A detection method employing the detection pad 10 according to the present embodiment will be described below. FIG. 3 is a diagram illustrating a state of a portable terminal photographing the detection pad 10 according to the present embodiment. Referring to FIG. 3, a user photographs a first reference area displayed in the first reference color, a second reference color patch, and a detection area of which a color is changed in response to a target (S100). As the embodiment, a portable terminal 20 of the user may be a smartphone including a camera module as shown in FIG. 3. In another embodiment not shown in the drawing, the portable terminal may be any one of a portable phone, a tablet, and a laptop.

The user may photograph the detection pad 10 using a camera provided in the portable terminal 20 and an application stored in the portable terminal 20. As an example, in the case of photography, the application may display a frame F corresponding to the quadrangle of the QR code 110 and a guide N that helps the user's photography.

The application converts a photography result into a single factor (S200). As an embodiment, an image captured by the user may be displayed with a red (R) value, a green (G) value, and a blue (B) value in an RGB color space, and the single factor may be any one of the R value, the G value, and the B value in the RGB color space. When the single factor is the R value, the application converts the image captured by the user only into the size of the R value.

The single factor may be a linear combination of the R value, the G value, and the B value. For example, when the R value, the G value, and the B value of one pixel included in the image captured by the user are r, g, and b, respectively, a single factor f may be a value represented as $f=\alpha \times r + \beta \times g + \gamma \times b$, and the application converts the image captured by the user into a size of $\alpha \times r + \beta \times g + \gamma \times b$.

In another embodiment, the single factor may be a grayscale value. The application may convert the image captured by the user to grayscale and display the converted image. For example, grayscale may be divided into 0 to 255 levels, a total of 256 levels.

As another embodiment, the single factor may be any one of a hue value, a saturation value, a value value, and a linear combination of the hue value, the saturation value, and the value value in the hue, saturation and value (HSV) color space. HSV is a color coordinate system that represents a color with hue, saturation, and value. Each pixel of the image captured by the user may be represented with hue, saturation, and value in the HSV color coordinate system, and the application may determine any one of the hue value, the saturation value, the value value, and a linear combination value thereof as the single factor and convert the image captured by the user into the single factor.

As still another embodiment, the single factor may be any one of linear combinations of a cyan value, a magenta value, a yellow value, and a key value in the cyan, magenta, yellow, and key (CMYK) color space. The result image captured by the user may be displayed with a cyan value, a magenta value, a yellow value, and a key value, and the application may determine any one of the cyan value, the magenta value, the yellow value, the key value, and a linear combination value thereof as the single factor and convert the image captured by the user into the single factor.

As yet another embodiment, the single factor may be an L* value, an a* value, and a b* value, and a linear combination of the L* value, the a* value, and the b* value in the CIELAB color space. The CIELAB color space is a color coordinate system that represents a color with L* having a value of black (0) to white (100), a* having a negative (−) value for green to a positive (+) value for red, and b* having a negative (−) value for blue to a positive (+) value for yellow. The application may determine any one of the L* value, the a* value, and the b* value, and the linear combination value thereof as the single factor and convert the image captured by the user with the size of the single factor.

In the above-described embodiments, when the single factor is calculated as a linear combination of factors, the constants α, β, and γ may be appropriately adjusted according to the range of calculated values of the factors. For example, when the single factor has a value of 0 to 255 and all of r, g, and b have a value of 0 to 255, all of the constants α, β, and γ may have a value of 0 to 1.

Figure 4:
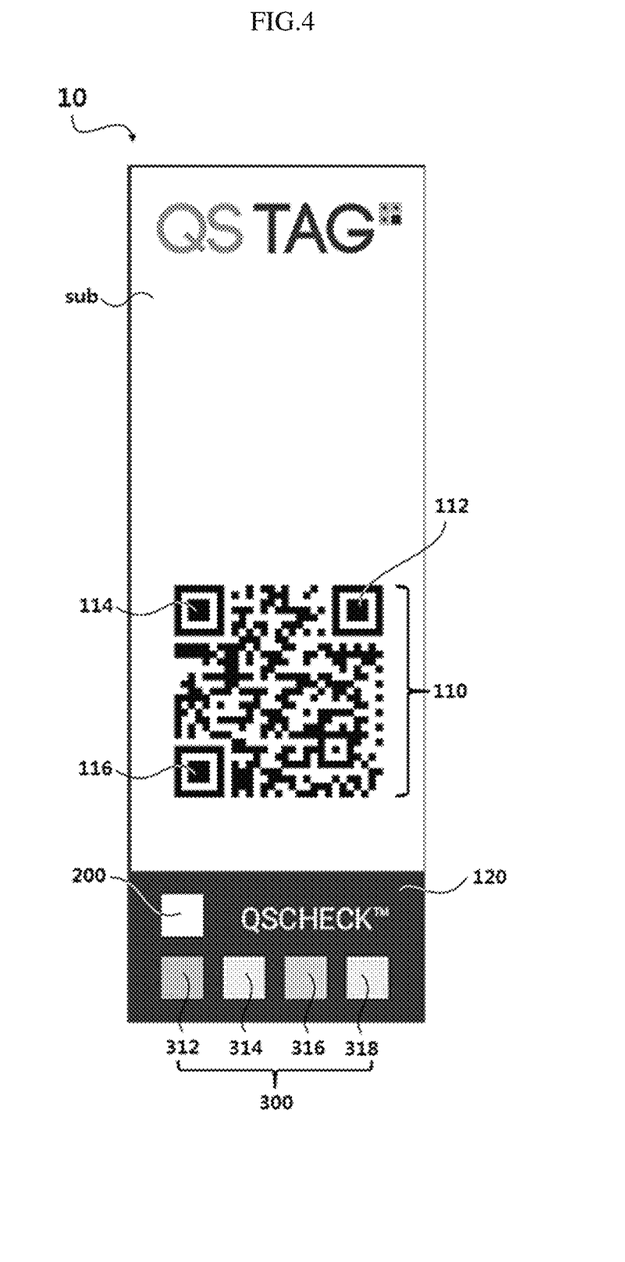
FIG. 4 is a diagram exemplifying a photography result converted into a single color tone.

An embodiment illustrated in FIG. 4 exemplifies a photography result converted into a single factor. However, FIG. 4 is a diagram exemplifying grayscale as the single factor, and a state in which the photography result is converted to grayscale may not be displayed to the user. As illustrated in FIG. 2, images of the first to fourth reagent patches 312, 314, 316, and 318 included in the detection area 300 may also be converted into the single factor.

Figure 5:
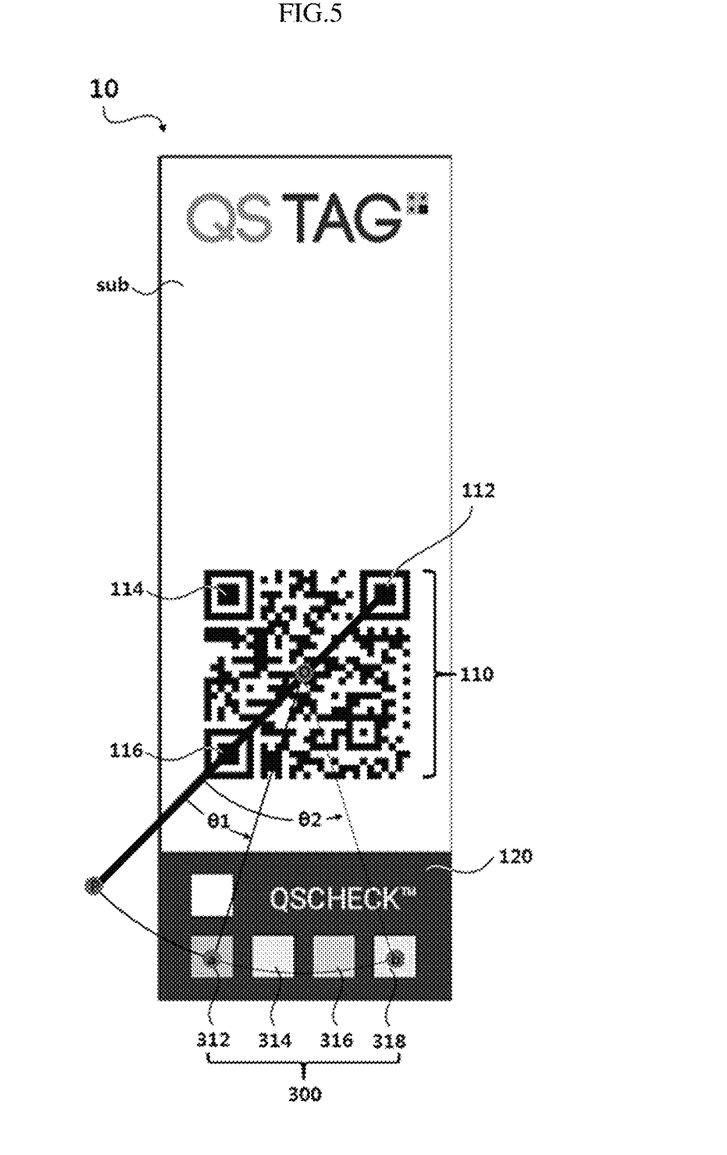
FIG. 5 is a diagram exemplifying a method of detecting a first reagent patch and a fourth reagent patch.

A single factor gradation value is extracted from the photography result converted into the single factor (S300). As the embodiment, the application may detect the location of the detection area 300 before extracting the single factor gradation value. Referring to FIG. 5, the application forms a center point O between the two orientation markers 112 and 116 diagonally located in the quadrangle of the QR code 110. Subsequently, a reference point P is formed at a distance corresponding to a predetermined ratio r of the length between the orientation markers from the center point O. A location a of the first reagent patch 312 included in the detection area 300 may be detected by rotating the reference point by a first angle θ1 with respect to the center point O.

Subsequently, a location b of the fourth reagent patch 318 included in the detection area 300 may be detected by rotating the reference point by a second angle θ2 with respect to the center point O. Also, the application may detect a location of the second reagent path 314 and a location of the third reagent patch 316 by trisecting the distance between the location a of the first reagent patch 312 and the location b of the fourth reagent patch 318.

In the embodiment, the application may form a second reference point at a distance corresponding to a predetermined ratio of the length between the center point O and the orientation marker and rotate the second reference point by a predetermined second angle with respect to the center point O to detect a location of the second reagent patch included in the detection area 300.

In the embodiment, the application may extract grayscale values of the single factor from a plurality of different points in the first reagent patch 312, the second reagent patch 314, the third reagent patch 316, and the fourth reagent patch 318. The application extracts grayscale values of the single factor from a plurality of points in the second reference color area 200, the first reference color area, and the first to fourth reagent patches 312 to 318.

Figure 6A:
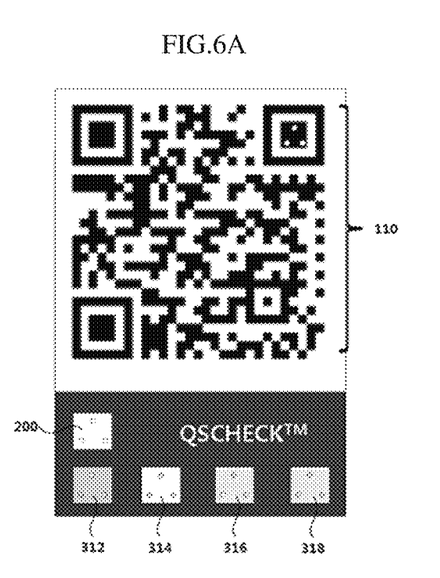
FIGS. 6A and 6B are diagrams schematically illustrating a part of the detection pad to describe a process in which an application obtains a gradation value.
Figure 6B:
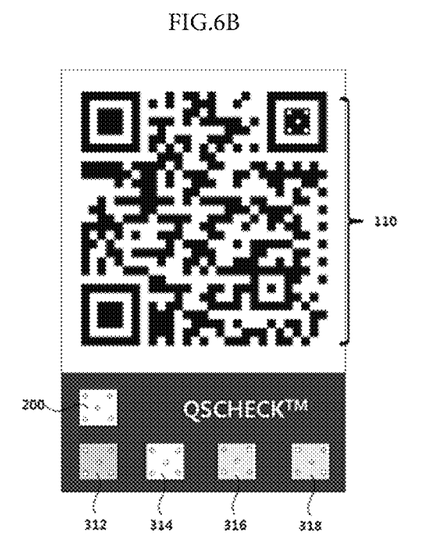

FIGS. 6A and 6B are diagrams schematically illustrating a part of the detection pad to describe a process in which the application obtains gradation values of the single factor from the second reference color area 200, the first reference color area, and the first to fourth reagent patches 312 to 318. In the embodiment shown in FIG. 6A, the application may obtain grayscale values of the single factor from a plurality of different points in the QR code 110 displayed in the first reference color, the first to fourth reagent patches 312 to 318, and the second reference color area 200 and average the grayscale values to extract a grayscale value of the single factor. In the embodiment shown in FIG. 6B, the application may obtain grayscale values of the single factor from a plurality of different points in the QR code 110 displayed in the first reference color, the first to fourth reagent patches 312 to 318, and the second reference color area 200 and average the grayscale values other than the maximum and the minimum to extract a grayscale value of the single factor.

The application corrects the extracted single factor grayscale value with standard grayscale values (S400). In the case of photographing the detection area 300, light reflected from the floor, the ceiling, and the wall may make a color cast on the first to fourth reagent patches 312 to 318, and artificial lighting, such as a fluorescent lamp light and incandescent lamp light, may make a color cast.

Also, when a fluid including the target is applied to the detection area 300, the colors of the reagent patches may be changed by the color of the fluid. For example, when the fluid is urine, the reagent patches may be colored yellow, and when the fluid is blood, the reagent patches may be colored red.

The application sets a grayscale value of the single factor extracted by photographing the second reference color area to 255 and sets a grayscale value of the single factor extracted by photographing the first reference color area to 0. The gradation values of the single factor captured in the first to fourth reagent patches 312 to 318 are converted into standard gradation values by scaling the extracted grayscale values of the single factor to a total of $2^{11}$ levels. As the embodiment, the application may perform a standard gradation value conversion using Equation 1. When n equals 8, $2^n-1$ equals 255, and standard gradation values have 0 to 255 levels, a total of 256 levels.

$$Ical = (2^n - 1)\frac{I_i - G1}{G2 - G1}$$

($L_{cal}$: a calculated standard gradation value, $I_i$: a gradation value of the single factor extracted in the previous step, $G_1$: a gradation value of the single factor extracted from the first reference color area, $G_2$: a gradation value of the single factor extracted from the second reference color area, n: a natural number)

Table 1 illustrates an example of converting gradation values I1, I2, I3, and I4 of the single factor extracted from the first to fourth reagent patches 312 to 318 and gradation values G1 and G2 of the single factor extracted from the first reference color area and the second reference color area into standard gradation values Ical1, Ical2, Ical3, Ical4, Gcal1, and Gcal2 when the gradation value G1 of the single factor extracted from the first reference color area is 15 and the gradation value G2 of the single factor extracted from the second reference color area is 231. As illustrated in Table 1, extracted gradation values of the single factor are converted into standard gradation values of 0 to 255 levels, a total of 256 levels.

TABLE 1

| Extracted gradation value | | Standard gradation value | |
| --- | --- | --- | --- |
| G1 | 15 | Gcal1 | 0 |
| G2 | 231 | Gcal2 | 255 |
| I1 | 175 | Ical1 | 183 |
| I2 | 195 | Ical2 | 212 |
| I3 | 134 | Ical3 | 152 |
| I4 | 125 | Ical4 | 135 |

The above example is for displaying a standard gradation value as 8-bit digital data, and as shown in (1) of Equation 2, standard gradation values may be obtained by dividing gradation values of the single factor, which are extracted by setting n to 10 in Equation 1, into 0 to 1023 levels, a total of 1024 levels. Alternatively, as shown in (2) of Equation 2, standard gradation values may be obtained by dividing gradation values, which are extracted by setting n to 6 in Equation 1, into 0 to 63 levels, a total of 64 levels. When standard gradation values divided into higher levels are used, standard gradation values having a higher resolution may be obtained, and when standard gradation values divided into lower levels are used, the calculation speed may be increased.

$$Ical = 1023 \frac{I_i - G1}{G2 - G1} \quad (1)$$

$$Ical = 63 \frac{I_i - G1}{G2 - G1} \quad (2)$$

A change in gradation value caused by color casts made by surroundings and a light source and influence of a color change caused by the color of a fluid may be removed. Likewise, a difference caused by the difference between a portable terminal and a camera module that take an image may be removed.

The application may detect a target concentration from the standard gradation value (S500). As the embodiment, the application detects the target concentration by calculating the concentration equation of a standard gradation value.

There may be a measurement difference in standard gradation according to a camera module included in a portable terminal that takes an image and/or an image processing algorithm of the portable terminal. As a method of reducing such a measurement difference, there is a method of deriving an equation regarding the concentration of a target for a standard concentration measurement value according to each terminal and measuring the concentration using the equation derived for each terminal. As another method, pieces of data may be collected from several types of portable terminals, and a type-specific measurement difference may be reduced using a result obtained by averaging the collected pieces of data.

Figure 7A:
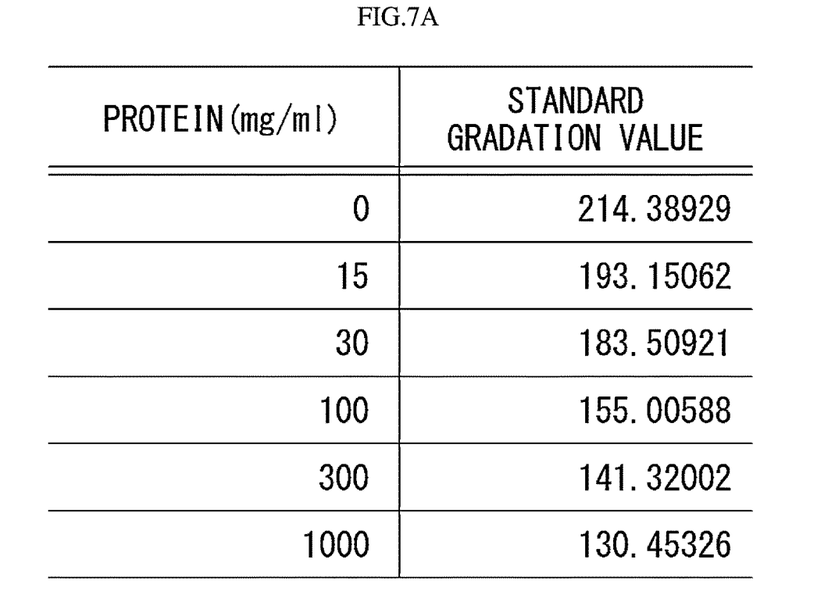
FIGS. 7A and 7B illustrate results obtained by measuring the concentrations (mg/ml) and standard gradation values of protein included in urine and a curve fitting result of the relationship between the concentrations (mg/ml) and standard gradation values of protein included in urine, respectively.
Figure 7B:
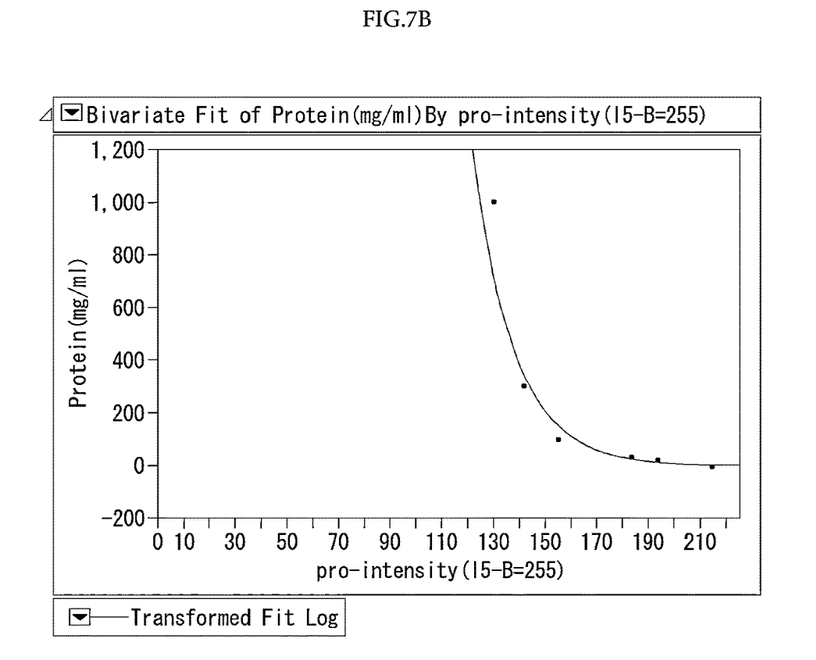

Equations 3 to 6 described below are results obtained by collecting pieces of data according to types of a plurality of domestic and foreign portable terminals and using a result obtained by averaging the collected pieces of data. FIGS. 7A and 7B illustrate results obtained by measuring the concentrations (mg/ml) and standard gradation values of protein included in urine and a curve fitting result of the relationship between the concentrations (mg/ml) and standard gradation values of protein included in urine, respectively. In FIGS. 7A and 7B, the horizontal axis represents standard gradation of 256 levels, and the vertical axis represents the concentration (mg/mi) of protein included in urine. The relationship between a target concentration obtained through an experiment and a standard gradation value may be obtained through a curve fitting process, and a curve fitting result equation for the relationship between the concentration (mg/mi) of protein included in urine and a standard gradation value is given below as Equation 3.

$$\ln(\text{protein}) = A - B \cdot Ical$$

(protein: the concentration of protein, Ical: a standard gradation value, A and B: constants determined through an experiment)

Figure 8A:
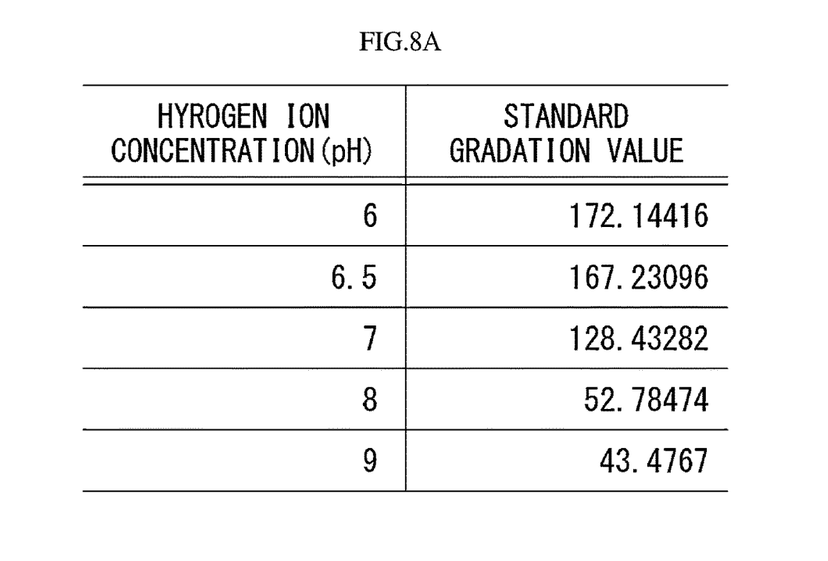
FIGS. 8A and 8B illustrate results obtained by measuring the concentrations (pH) and standard gradation values of hydrogen ions included in urine and a curve fitting result of the relationship between the concentrations (pH) and standard gradation values of hydrogen ions included in urine, respectively.
Figure 8B:
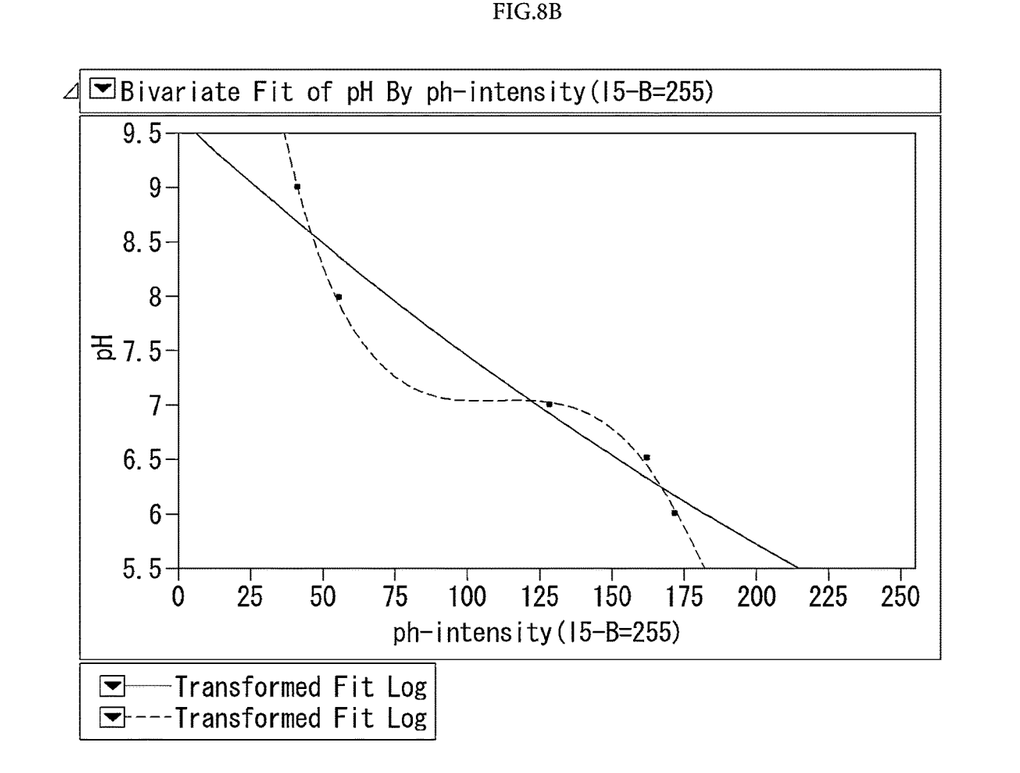

FIGS. 8A and 8B illustrate results obtained by measuring the concentrations (pH) and standard gradation values of hydrogen ions included in urine and a curve fitting result of the relationship between the concentrations (pH) and standard gradation values of hydrogen ions included in urine, respectively. In FIG. 8, the horizontal axis represents standard gradation of 256 levels, and the vertical axis represents the concentration (pH) of hydrogen ions. The relationship between a target concentration obtained through an experiment and a standard gradation value may be obtained through a curve fitting process, and a linear fitting result equation for the relationship between the concentration (pH) of hydrogen ions included in urine and a standard gradation value is given below as Equation 4.

$$\ln(pH) = C + D \cdot Ical - E(Ical - F)^2 - G(Ical - H)^3$$

(C, D, E, F, G, and H: constants determined through an experiment)

Figure 9A:
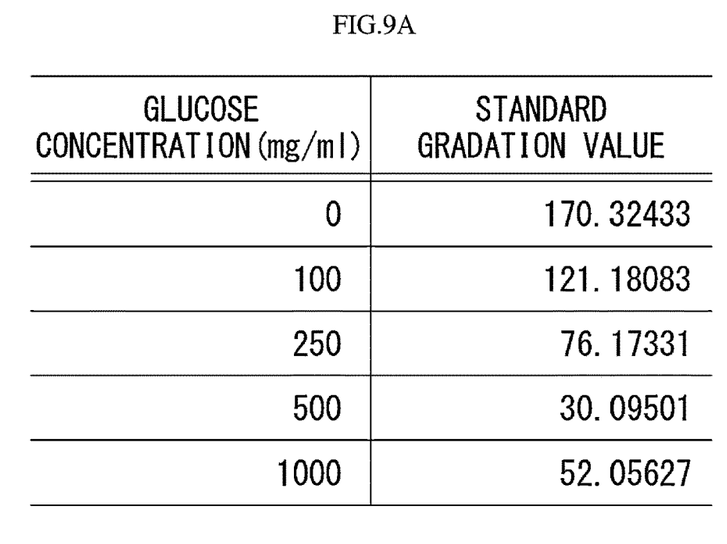
FIGS. 9A and 9B illustrate results obtained by measuring the concentrations (mg/ml) and standard gradation values of glucose included in urine and a curve fitting result of the relationship between the concentrations (mg/ml) and standard gradation values of glucose included in urine, respectively.
Figure 9B:
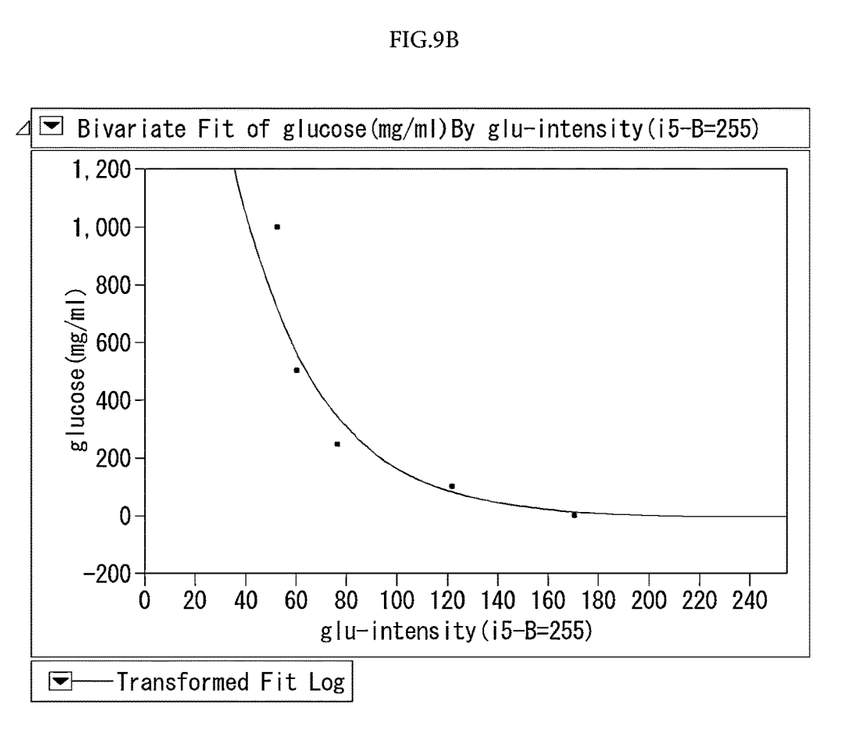

FIGS. 9A and 9B illustrate results obtained by measuring the concentrations (mg/ml) and standard gradation values of glucose included in urine and a curve fitting result of the relationship between the concentrations (mg/ml) and standard gradation values of glucose included in urine, respectively. In FIG. 9, the horizontal axis represents standard gradation of 256 levels, and the vertical axis represents the concentration (mg/ml) of glucose. The relationship between a target concentration obtained through an experiment and a standard gradation value may be obtained through a curve fitting process, and a curve fitting result equation for the relationship between the concentration (mg/mi) of glucose included in urine and a standard gradation value is given below as Equation 5.

$$\ln(\text{Glucose}) = I - J \cdot Ical$$

(I and J: constants determined through an experiment)

Figure 10A:
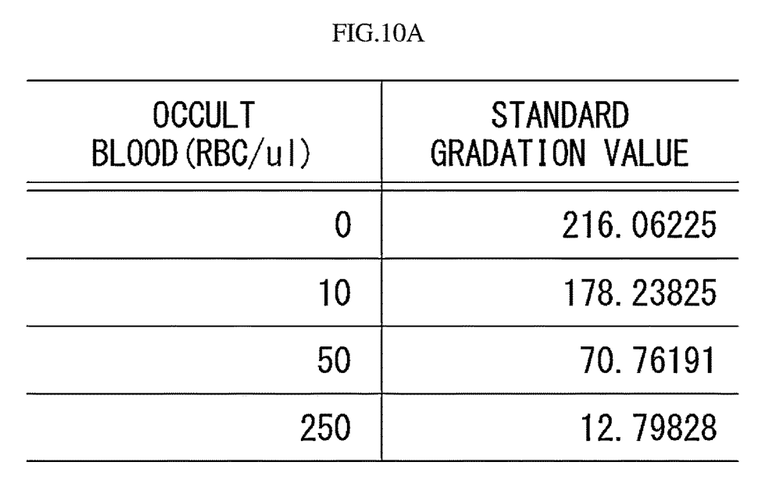
FIGS. 10A and 10B illustrate results obtained by measuring occult blood (red blood cell (RBC)/µl) included in urine and standard gradation values and a curve fitting result of the relationship between the occult blood (RBC/µl) included in urine and standard gradation values, respectively.
Figure 10B:
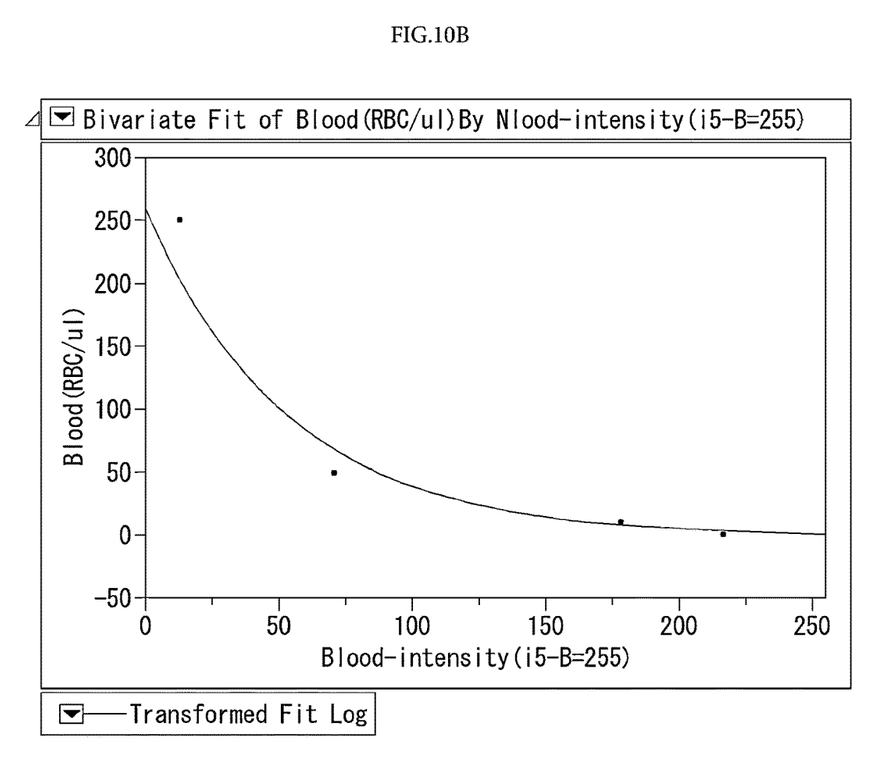
Figure 11:
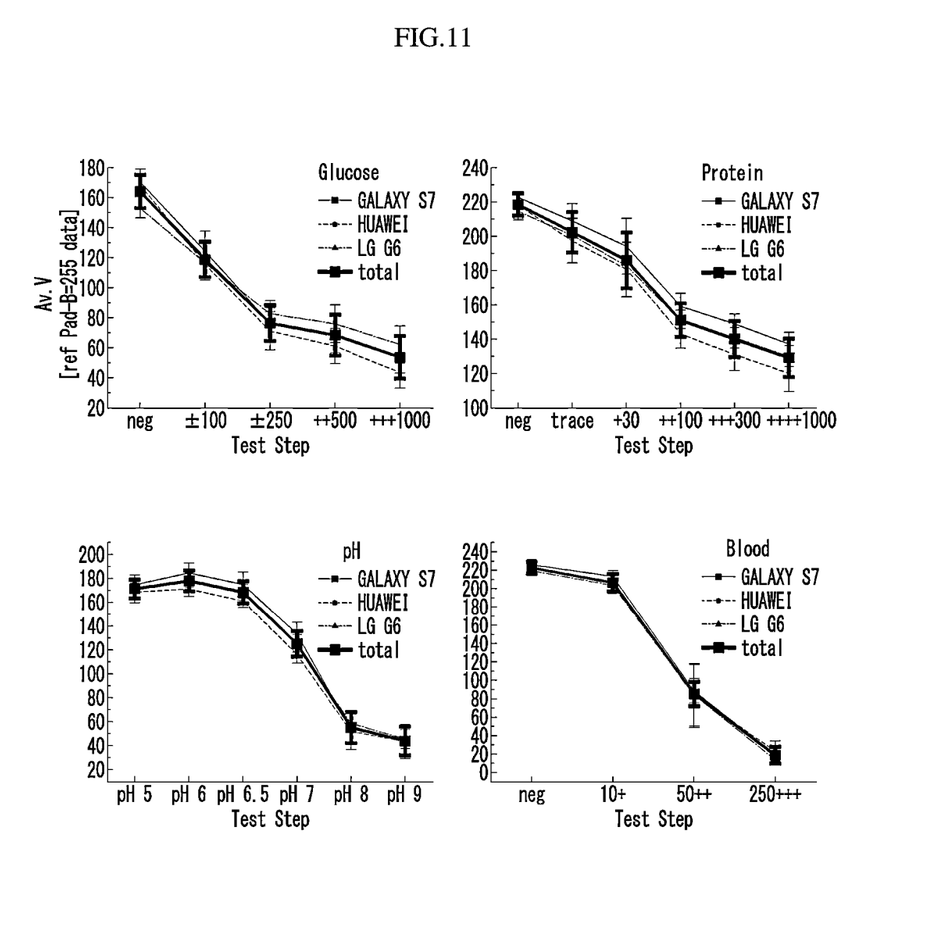
FIG. 11 is a set of diagrams illustrating differences between the types of portable terminals that take an image.

FIGS. 10A and 10B illustrate results obtained by measuring occult blood (red blood cell (RBC)/μl) included in urine and standard gradation values and a curve fitting result of the relationship between the occult blood (RBC/μl) included in urine and standard gradation values, respectively. In FIG. 10, the horizontal axis represents standard gradation of 256 levels, and the vertical axis represents the occult blood (RBC/μl). The relationship between a target concentration obtained through an experiment and a standard gradation value may be obtained through a curve fitting process, and a linear fitting result equation for the relationship between occult blood (RBC/μl) included in urine and a standard gradation value is given below as Equation 6.

$$\ln(\text{Blood}) = K - L \cdot Ical$$

(K and L: constants determined through an experiment)

In another embodiment of detecting the concentration of a target, the application may store concentration values of the target with respect to standard gradation values. The application may detect the stored concentration of the target with a calculated standard gradation value. As the embodiment, the application may calculate the stored concentration value of the target with a standard gradation value through interpolation or extrapolation and determine the calculation result as the concentration of the target.

Although the present invention has been described with reference to embodiments illustrated in the drawings to aid in understanding, the embodiments are for implementation and merely illustrative. Those of ordinary skill in the art should appreciate that various modifications and equivalents can be can be made from the embodiments. Therefore, the technical scope of the present invention should be determined by the appended claims.

The invention claimed is:

1. A detection method comprising:
   (a) photographing a first reference color area displayed in a first reference color, a second reference color area displayed in a second reference color, and a detection area of which a color is changed in response to a target;
   (b) converting a photography result into a single factor;
   (c) extracting a single factor gradation value from the converted photography result;
   (d) converting the extracted single factor gradation value into a standard gradation value; and
   (e) detecting a concentration of the target from the standard gradation value.

2. The detection method of claim 1, wherein operation (c) is performed by calculating an average single factor gradation value of a plurality of different points in each of the first reference color area, the second reference color area, and the detection area.

3. The detection method of claim 1, wherein operation (d) comprises:
   (d1) scaling a single factor gradation value of the first reference color to 0 and a single factor gradation value of the second reference color area to $2^n-1$ (n is a natural number greater than 4); and
   (d2) adjusting a single factor gradation value extracted from the detection area according to results of operation (d1).

4. The detection method of claim 1, wherein operation (b) is performed by converting the photography result to grayscale.

5. The detection method of claim 1, wherein operation (b) is performed by converting the photography result into any one selected from the group consisting of any one of a red (R) value, a green (G) value, a blue (B) value, and a linear combination of the R value, the G value, and the B value in a red-green-blue (RGB) color space, any one of a hue value, a saturation value, a value value, and a linear combination of the hue value, the saturation value, and the value value in a hue saturation value (HSV) color space, any one of a cyan value, a magenta value, a yellow value, a key value, and a linear combination of the cyan value, the magenta value, the yellow value, and the key value in a cyan magenta yellow key (CMYK) color space, and any one of an L* value, an a* value, a b* value, an L* value, and a linear combination of the L* value, the a* value, and the b* value in a CIELAB color space.

6. The detection method of claim 1, wherein operation (e) comprises detecting the target concentration by calculating a concentration equation for standard gradation values with the standard gradation value obtained in operation (d).

7. The detection method of claim 6, wherein the concentration equation for standard gradation values is derived from averages of the standard gradation values acquired from types of devices with which photography is performed in operation (a).

8. The detection method of claim 6, wherein the concentration equation for standard gradation values corresponds to a type of device with which photography is performed in operation (a).

9. The detection method of claim 1, wherein operation (e) comprises detecting the concentration of the target with respect to the standard gradation value by searching a memory, in which the target concentration is stored in connection with a standard gradation value, with the standard gradation value obtained in operation (d).

10. The detection method of claim 9, wherein the standard gradation value corresponds to a type of device with which photography is performed in operation (a).

11. The detection method of claim 9, wherein the standard gradation value is an average of standard gradation values acquired from a plurality of types of devices with which photography of operation (a) is performed.

12. The detection method of claim 1, wherein the first reference color area is a quick response (QR) code of a quadrangle having three vertices at which orientation markers are displayed, and
   operation (c) comprises:
   (c1) forming a center point between the two orientation markers diagonally located in the quadrangle;
   (c2) forming a reference point at a distance corresponding to a predetermined ratio of a length between the orientation markers from the center point; and
   (c3) detecting the detection area by rotating the reference point by a predetermined first angle with respect to the center point.

13. The detection method of claim 12, wherein the detection area includes a first reagent patch, a second reagent patch, a third reagent patch, and a fourth reagent patch, and the detection method detects the first reagent patch by performing operation (c3) and further comprises:
   (c4) detecting the fourth reagent patch by rotating the reference point by a predetermined second angle with respect to the center point; and
   (c5) detecting the second reagent patch and the third reagent patch by trisecting a distance between the detected first reagent patch and second reagent patch.

14. A detection pad for testing a target in a fluid, the detection pad comprising:
   a machine-readable code displayed in a first reference color;
   a second reference color area used for removing an influence of a color change caused by the fluid; and
   reagent patches, each including a reagent of which a color is changed in response to the target,
   wherein the machine-readable code is a quick response (QR) code of a quadrangle having three vertices at which orientation markers are displayed, and
   wherein the detection pad further comprises:
   a center point between two orientation markers diagonally located in the quadrangle,
   a reference point at a distance corresponding to a predetermined ratio of a length between the orientation markers from the center point; and
   all the reagent patches of the detection pad located in detection area, along an arc defined by rotating the reference point by a first angle θ1 and a second angle θ2 with respect to the center point located within a display of the machine-readable code.

15. The detection pad of claim 14, wherein the first reference color is black, and
the second reference color is white.

16. The detection pad of claim 14, wherein the machine-readable code displays information on a number of reagent patches included in the detection pad and classification information of the detection pad.

17. The detection pad of claim 14, wherein the fluid is a body fluid of any one of a human or an animal.

18. The detection pad of claim 14, wherein the detection area includes a plurality of reagent patches.

19. The detection pad of claim 18, wherein each of the plurality of reagent patches includes a reagent of which a color is changed according to glucose in the fluid, protein in the fluid, hydrogen ions in the fluid, occult blood in the fluid, bilirubin in the fluid, urobilinogen in the fluid, ketone bodies in the fluid, nitrides in the fluid, a specific gravity of the fluid, and white blood cells in the fluid.

20. The detection pad of claim 14, wherein the detection area includes a first reagent patch, a second reagent patch, a third reagent patch, and a fourth reagent patch.

\* \* \* \* \*